United States Patent
Röder

(10) Patent No.: US 10,265,541 B2
(45) Date of Patent: Apr. 23, 2019

(54) FOR SIMPLIFIED REMOVAL OF A BALLOON APPLICATOR

(71) Applicant: Carl Zeiss Meditec AG, Jena (DE)

(72) Inventor: Norman Röder, Aalen (DE)

(73) Assignee: CARL ZEISS MEDITEC AG, Jena (DE)

(*) Notice: Subject to any disclaimer, the term of this patent is extended or adjusted under 35 U.S.C. 154(b) by 318 days.

(21) Appl. No.: 14/952,497

(22) Filed: Nov. 25, 2015

(65) Prior Publication Data
US 2016/0151643 A1    Jun. 2, 2016

(30) Foreign Application Priority Data
Nov. 27, 2014   (DE) .................. 10 2014 117 430

(51) Int. Cl.
*A61N 5/10*    (2006.01)

(52) U.S. Cl.
CPC ......... *A61N 5/1007* (2013.01); *A61N 5/1014* (2013.01); *A61N 2005/1008* (2013.01); *A61N 2005/1022* (2013.01)

(58) Field of Classification Search
CPC .......... A61N 5/1007; A61N 2005/1008; A61N 2005/1022; A61N 5/1014
See application file for complete search history.

(56) References Cited

U.S. PATENT DOCUMENTS

| | | | |
|---|---|---|---|
| 5,621,780 A | 4/1997 | Smith et al. | |
| 7,382,857 B2 | 6/2008 | Engel | |
| 2002/0133217 A1* | 9/2002 | Sirhan | A61M 25/10 623/1.11 |
| 2005/0080313 A1 | 4/2005 | Stewart et al. | |
| 2005/0080340 A1 | 4/2005 | Stewart et al. | |
| 2006/0126789 A1 | 6/2006 | Dinsmore et al. | |
| 2010/0331878 A1 | 12/2010 | Kleinwachter | |
| 2011/0071506 A1 | 3/2011 | Gardner et al. | |

FOREIGN PATENT DOCUMENTS

| | | |
|---|---|---|
| WO | WO 97/37714 A1 | 10/1997 |
| WO | WO 01/12255 A1 | 2/2001 |

OTHER PUBLICATIONS

European Search Report (Application No. 15195892.3) dated Aug. 31, 2016.

* cited by examiner

*Primary Examiner* — Christine H Matthews
*Assistant Examiner* — Joshua Daryl D Lannu
(74) *Attorney, Agent, or Firm* — Nixon Peabody LLP; Jeffrey L. Costellia

(57) ABSTRACT

A balloon applicator for irradiation of a cavity within living tissue is provided, comprising a double-lumen shaft and with a balloon connected to the shaft at a proximal and a distal position, in which a movement of a first portion of the shaft relative to a second portion of the shaft can be effected. In addition, a tool is provided which can be inserted into a lumen of the shaft and which is designed to effect the relative movement. Furthermore, a system is provided composed of balloon applicator and tool.

18 Claims, 2 Drawing Sheets

FOR SIMPLIFIED REMOVAL OF A BALLOON APPLICATOR

The invention relates to a balloon applicator for irradiation of a cavity within living tissue, in which the balloon can be laid around or upon the applicator shaft within the living tissue.

Intraoperative radiation therapy (IORT) of living tissue is a treatment method that is used in particular after surgical removal of a tumor. The balloon applicator is typically composed of a shaft, wherein a balloon is arranged at the proximal end of the shaft. The shaft serves to provide the radiation source with access to the center of the balloon, in order to irradiate the tumor bed from within, and to introduce a medium for filling the balloon. The radiation source is, for example, an X-ray source (U.S. Pat. No. 5,621,780). The applicator is guided through the skin and the tissue as far as the tumor bed, where the balloon is deployed by being filled with a medium, typically a fluid, particularly a saline solution or a gas. The deployed balloon guarantees the position and size of the tumor bed relative to the radiation source during the irradiation, since the tumor bed would otherwise collapse (WO2005/037363, WO2006/041733, WO2006/065299, WO2006/061722).

The balloon can be made of extensible material, e.g. silicone, as a result of which the balloon size depends on the volume of the filling medium. A disadvantage of this, however, is the possibility of the balloon being deformed by mechanical forces from outside.

The balloon can also be made of non-extensible material, e.g. polyethylene terephthalate (PET) or polyurethane (PUR), which ensures a discrete balloon shape and size, as a result of which the shape of the cavity of the tumor bed can be maintained. The problem of using non-extensible materials lies in the folding of the balloon prior to removal from the patient. It is possible to remove the balloon from the corresponding tissue cavity by means of special devices (US2010/0331878). Alternatively, the balloon together with the shaft can be pulled out of the tissue cavity and therefore through the surrounding tissue. However, when the filling medium is aspirated, the balloon forms folds, which are more or less pronounced depending on the size of the balloon. Outside the body, such folds can be laid around the shaft of the balloon applicator, i.e. prior to the insertion of the balloon applicator for the minimally invasive procedure the balloon of the balloon applicator can be laid around the shaft such that the balloon applicator can be guided to the tumor bed without any appreciable resistance. Inside the body, i.e. after deployment of the balloon by filling and emptying, this is impossible on account of the more difficult accessibility. If the balloon when emptied, but not laid around the shaft, is pulled through the tissue, e.g. through a biopsy channel, to outside of the body, this poses a danger of trauma and damage to the tissue.

Moreover, if there is a defect of the hose system, it can happen that the balloon cannot be emptied and, consequently, remains in the tissue cavity after irradiation has been performed. This can mean that the balloon applicator has to be removed surgically, which places an unnecessary burden on the patient.

The object is therefore to provide a balloon applicator whose balloon, inside a tissue cavity, can be laid around or upon the shaft in such a way that it can be pulled with minimal force through the tissue out of the tissue cavity.

This object is achieved with a balloon applicator according to claim 1. Further advantageous embodiments are set forth in the additional independent claims, the dependent claims, the figures and the illustrative embodiments.

A first aspect of the invention relates to a balloon applicator for irradiation of a cavity within living tissue, comprising an at least double-lumen shaft with a first lumen for introduction of a medium for filling a balloon connected to the shaft at a proximal and a distal position thereof, and with a second lumen for insertion of a radiation source, in which the shaft, between the proximal and the distal position, has a proximally arranged first portion and a distally arranged second portion which, in a first working state of the balloon applicator, are connected to each other and, in a second working state of the balloon applicator, are separated from each other.

The balloon applicator according to the invention is advantageous because, in the first working state, it permits the introduction and application of radiation of a tissue cavity and because, in the second working state, its folds of its balloon, within a body cavity, can be laid around or upon the shaft by control from outside, as a result of which the balloon applicator can be removed without causing unnecessary trauma to the tissue of the patient. Moreover, the balloon applicator according to the invention is advantageous because, by rotating the shaft parts relative to each other, the filling medium can optionally be pressed out if the balloon cannot be emptied on account of a defect of the hose system.

It is preferable if the first portion of the shaft of the balloon applicator comprises the proximal position and the second portion of the shaft comprises the distal position, at which the balloon is respectively secured on the shaft. Advantageously, on account of the connection of the balloon to the shaft at the distal and the proximal position, the balloon can be laid around or upon the shaft during a movement of the first portion of the shaft about its axis relative to the second portion of the shaft.

It is moreover preferable if the shaft of the balloon applicator, in a boundary section between the first and the second portion of the shaft, has a predetermined breaking point, which is designed to break when a defined longitudinal force and/or a torsional moment are/is exceeded. Preferably, the predetermined breaking point is located at the boundary between the first and the second part of the shaft. The boundary between the first and the second part of the shaft is to be considered as a portion of the shaft lying at an equal distance from each of the ends of the first and second part, i.e. lying approximately at the middle between these ends. At the predetermined breaking point, the material of the shaft has properties which, upon application of a force, permit easier breaking of the material than in other areas of the shaft. A shaft with a predetermined breaking point is advantageous because the proximal and distal parts are thereby movable relative to each other and the balloon, in an empty state inside a body, can be laid around the shaft or upon the shaft. A further advantage is that the breaking of the rigid shaft part at the predetermined breaking point prevents multiple use of the balloon applicator, which is provided as a throw-away product, since it can then no longer be inserted into the body.

It is moreover preferable if the shaft of the balloon applicator, in a boundary section between the first and the second portion, has a connection with a thread. A thread, e.g. a screw connection, advantageously permits a rotational movement of the portions relative to each other, and also a simultaneous movement of the portions relative to each other in a longitudinal direction and a rotational direction.

By the combination of rotational movement and linear movement, the balloon can be laid both around and also upon the shaft.

It is moreover preferable if the shaft of the balloon applicator, in the boundary section between the first portion and the second portion, has a seal which is designed to seal the first and second lumen of the shaft in the second working state of the balloon applicator.

In a preferred embodiment, a tool can additionally be inserted into the second lumen of the balloon catheter, which tool is designed to apply at least one force to the first portion of the shaft and/or the second portion of the shaft. By means of the tool, the portions of the shaft can be comfortably separated from each other and moved relative to each other, as a result of which the balloon can advantageously be laid around the shaft. The balloon can also be laid around the shaft manually, i.e. without a tool, for example by the end protruding from the patient being rotated after the first and second portions of the shaft have been separated from each other.

Preferably, the second or first portion of the shaft can be fixed by the tool, and a torsional moment acting relative to the second or first portion of the shaft in a rotational direction about the longitudinal axis of the first portion can be applied by the tool to the first or second portion of the shaft. It is also preferable if the first or second portion of the shaft can be fixed by the tool, and a force acting relative to the first or second portion of the shaft in the longitudinal direction of the shaft can be applied by the tool to the second or first portion of the shaft. It is also possible for both portions to be movable by means of the tool in the rotational direction about their respective longitudinal axis, specifically in opposite directions to each other. Moreover, it is also possible for both portions to be moved by means of the tool in mutually opposite longitudinal directions.

A combination of rotation of the parts about the longitudinal axis of the shaft and of linear movement thereof, i.e. movement in the longitudinal direction of the shaft, is also possible. The combination of rotational movement and linear movement is advantageous because in this way the balloon is laid both around the shaft and also upon the shaft, and the folds of the balloon are thus more effectively drawn smooth.

Preferably, the second lumen of the shaft has at least one depression or protuberance in which the tool engages with a form fit via at least one protuberance or depression. This has the advantageous effect that the tool can engage with the shaft in a form-fit manner according to a key and lock principle. If the tool has a multi-part design, one part of the tool with a depression or protuberance matches a protuberance or depression of the first part of the shaft with a form fit, and another part of the tool correspondingly matches the second part of the shaft with a form fit. Thus, one part of the shaft can be fixed while the other is moved. In this way, for example, a rotational movement of one part is permitted relative to the other part of the shaft.

The second lumen of the shaft of the balloon applicator preferably has at least one holding point for receiving the tool. A first holding point is preferably located at the proximal end of the shaft in the second lumen, i.e. in the first part of the shaft. The first holding point is advantageously designed such that a part of the tool can be pressed against it, i.e. the tool can apply a force acting in the proximal longitudinal direction of the shaft.

A second holding point is preferably located in the second part of the shaft in the second lumen and is designed such that the tool can be applied there in order to exert a tensile force in the distal direction, i.e. a force acting in the distal longitudinal direction of the shaft. Preferably, the first holding point and the second holding point have protuberances or depressions in which the tool engages with a form fit via corresponding depressions or protuberances.

By way of the first and second holding points, the tool can effect relative movements of the first part of the shaft relative to the second part of the shaft in the longitudinal direction, as a result of which the distance between the proximal and distal connections of the balloon to the shaft can be increased. The balloon can thus be drawn smooth in the longitudinal direction of the shaft and thus laid upon the shaft.

Preferably, a part of the tool can be fixed on the first holding point. By means of another part of the tool which can be connected at the second holding point in the second lumen of the shaft, a force acting in the distal longitudinal direction of the shaft can be applied. The balloon is thus pulled in the distal direction, as a result of which a relative movement of the second part of the shaft relative to the first part of the shaft in the longitudinal direction can be effected, as a result of which the distance between the proximal and distal connections of the balloon can be increased, and the balloon can thus be drawn smooth along the shaft.

It is likewise preferable that a part of the tool can be fixed on the second holding point at the distal end, and another part of the tool can be connected to the first holding point, in order to exert a force acting in the proximal direction and thereby to increase the distance between the proximal and distal connections of the balloon and draw the balloon smooth. It is also possible to apply a tensile force to the second holding point and a pressure force to the first holding point simultaneously, in order to increase the distance between the proximal and distal connections of the balloon and to draw the balloon smooth.

Moreover, the balloon applicator has both depressions and/or protuberances in which the tool engages with a form fit, in order to effect a rotational movement of the first or second part of the shaft relative to the second or first, and also holding points for the tool, in order to effect a longitudinal movement of the first or second part of the shaft relative to the second or first. This embodiment is advantageous since it permits relative rotational and longitudinal movements of the shaft parts, which movements can be executed both simultaneously and also in succession. In other words, it is preferable if the tool and the lumen of the shaft have matching depressions and protuberances which permit both a rotational movement about the longitudinal axis of the shaft and also longitudinal movements along the longitudinal axis of the shaft.

It is moreover preferable if the balloon applicator according to the invention has a rigid portion and a flexible portion. The rigid portion is the one which is inserted into the tissue cavity and on which the balloon is secured. The first and second parts of the balloon with the balloon connections are accordingly enclosed by the rigid portion. The flexible part is intended to be located partially, for example, in a biopsy channel, through which the balloon applicator was brought into the tissue cavity, and partially outside the body; it serves for handling the balloon applicator.

A second aspect of the invention relates to a tool for applying a force to the first portion of the shaft and/or the second portion of the shaft of the balloon applicator according to the invention, which tool has an outer tube and has an inner core mounted movably in the outer tube. After the removal of the radiation source from the second lumen, the tool can be inserted into the second lumen and is movable in the latter in the longitudinal direction.

The outer tube and the inner core of the tool can be made of any possible material that permits use in a tissue cavity. Moreover, the outer tube and the inner core of the tool can be made from the same material, although they can also have different materials.

The outer tube and the inner core of the tool are advantageously rod-shaped. The rod-shaped design permits the insertion into the second lumen of the balloon applicator and also the fixing and moving of the first and second portions of the shaft by the tool.

The outer tube of the tool has at least one protuberance or depression which, with a form fit, match at least one depression or protuberance in the second lumen of the balloon applicator. This advantageously has the effect that, in the shaft interior, the outer tube can engage with the second portion of the shaft in a form-fit manner according to a key and lock principle.

The inner core of the tool has at least one protuberance or depression which, with a form fit, match at least one depression or protuberance in the second lumen of the balloon applicator. This advantageously has the effect that, in the shaft interior, the inner core can engage with the first portion of the shaft in a form-fit manner according to a key and lock principle.

A third aspect of the invention relates to a system composed of the balloon applicator according to the invention and of the tool according to the invention. In the system, the tool can advantageously be moved in the second lumen of the shaft of the balloon applicator after the radiation source has been removed. By means of the tool, it is advantageously possible to separate the first and second portions of the shaft from each other and to move the first and second parts of the shaft relative to each other.

A fourth aspect of the invention relates to a method for smoothing folds of a balloon arranged on the shaft of a balloon applicator within living tissue, wherein a first part of the shaft is moved relative to a second part of the shaft and the balloon is laid around or upon the shaft of the balloon applicator. Preferably, after removal of a radiation source from a second lumen of the balloon applicator, a tool is inserted into the second lumen of the balloon applicator. A first portion of the shaft of the balloon applicator is fixed by the tool, and a force is applied to a second portion. This preferably has the effect that a predetermined breaking point provided in the shaft of the balloon applicator breaks, as a result of which a relative movement of the second part with respect to the first part of the tool is permitted. The second portion is then moved relative to the first portion by means of the tool. The movement can take place in a rotational direction about the and/or along the longitudinal axis of the shaft of the balloon applicator. Alternatively, the balloon folds can also be laid around or upon the shaft without a tool, by means of the portion protruding from the body being manually rotated from the outside. This likewise preferably causes the predetermined breaking point to break.

By means of the relative movement of the portions by rotation and/or longitudinal movement of the portions of the shaft, the balloon is laid around the shaft and/or is laid upon the shaft along the shaft. If the connection between the first part and the second part of the shaft is in the form of a thread turn, a rotational movement about the longitudinal axis of the shaft and a longitudinal movement along the longitudinal axis of the shaft are effected simultaneously, as a result of which the balloon is simultaneously wound around the shaft and laid upon the shaft along the shaft.

The invention is explained in more detail with reference to the figures, in which.

Figure 1:
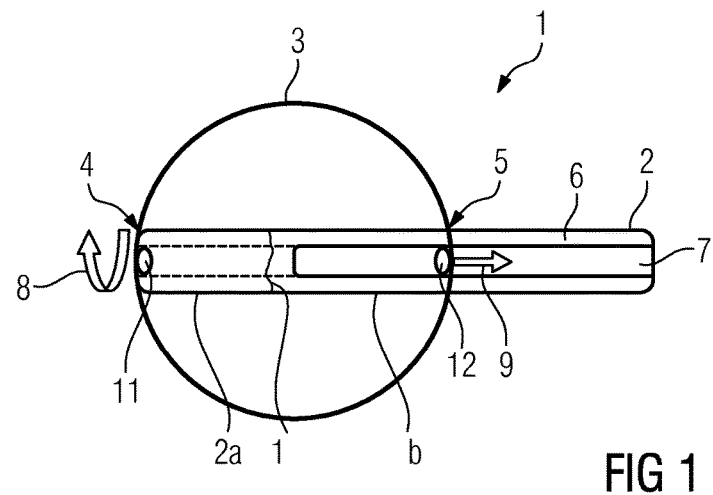
FIG. 1 shows an illustrative embodiment of a balloon applicator according to the invention in cross section.

The illustrative embodiment, shown in FIG. 1, of the balloon applicator 1 according to the invention for irradiation of a cavity within living tissue comprises an at least double-lumen shaft 2, a balloon 3 connected to the shaft 2 at a proximal 4 and a distal position 5 thereof, a first lumen 6 for introduction and discharge of a medium for filling the balloon 3, and a second lumen 7 for insertion of a radiation source, wherein a tool 30 can additionally be inserted through the second lumen 7 after removal of the radiation source, which tool 30 is designed to effect a movement of a proximally arranged first portion of the shaft 2a relative to a distally arranged second portion of the shaft 2b. The shaft 2 has a predetermined breaking point 10 at which the material of the shaft 2 between first portion 2a and second portion 2b can be broken and, consequently, the connection between the two parts of the shaft 2 can be undone. In an alternative embodiment, instead of the predetermined breaking point 10, a connection can be provided by a thread turn, i.e. e.g. by a screw connection. Moreover, a magnetic connection between the first portion 2a and second portion 2b is also possible. In the second lumen 7, a first holding point 11 for receiving the tool 30 is arranged proximally, and a second holding point 12, which likewise serves to receive the tool 30, is arranged distally.

Figure 2:
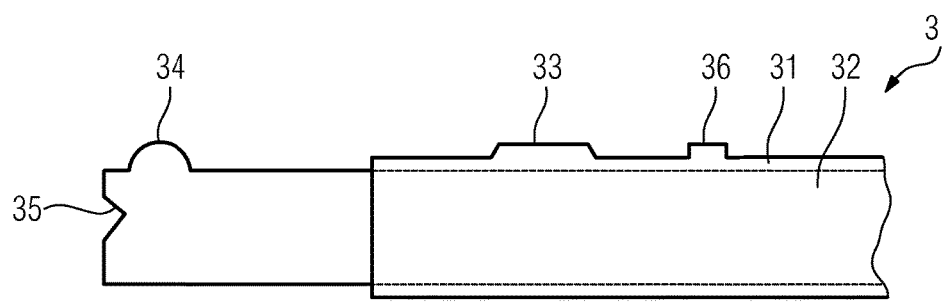
FIG. 2 shows an illustrative embodiment of a tool according to the invention in cross section.

The tool 30 shown in FIG. 2 is composed mainly of an outer tube 31 and of an inner core 32. The inner core is mounted movably in the outer tube 31. In a greatly simplified form, the tool 30 can also be a rod that can be moved inside the second lumen 7 in the longitudinal direction. The outer tube 31 has protuberances 33 and 36, and the inner core 32 has a protuberance 34 and a depression 35.

Figure 3:
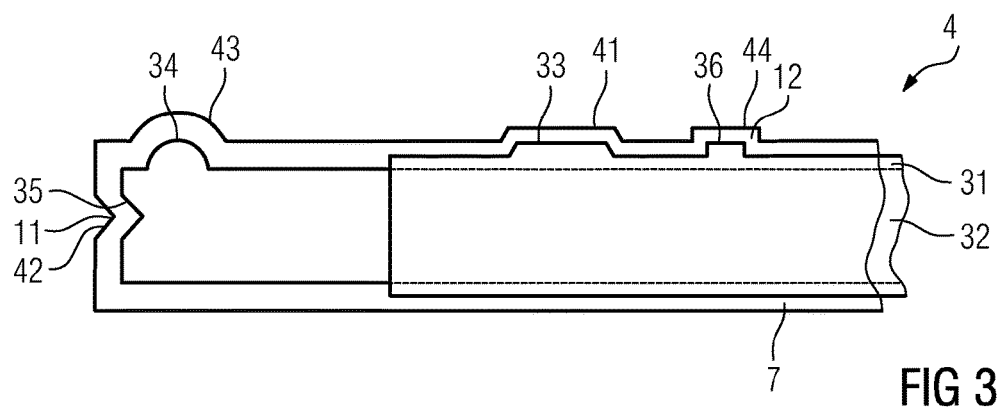
FIG. 3 shows an illustrative embodiment of a system according to the invention in cross section.

FIG. 3 shows a system 40 formed by the balloon applicator 1 and the tool 30. The outer tube 31 has a protuberance 33, which engages with a form fit in a depression 41 in the material of the second lumen 7. The inner core 32 has a protuberance 34, which engages with a form fit in a depression 43 in the material of the second lumen 7. The protuberances in the tool 30 and depressions in the second lumen 7 ideally correspond in number to each other. It is also possible for depressions to be present in the tool 30 and for protuberances to be present in the second lumen 7. It is also possible for both protuberances and also depressions to be present in the tool 30 and in the second lumen 7. Tool 30 and shaft 2 have at least one protuberance or depression, which can have any suitable shape, e.g. can be round or polygonal, square or elongate, wherein an elongate, groove-like configuration is preferred. The protuberances and depressions can expediently be present in any desired number, preferably 1-10, likewise preferably 2-9, likewise preferably 3-8, likewise preferably 4-7, and likewise preferably 5 or 6.

Figure 4:
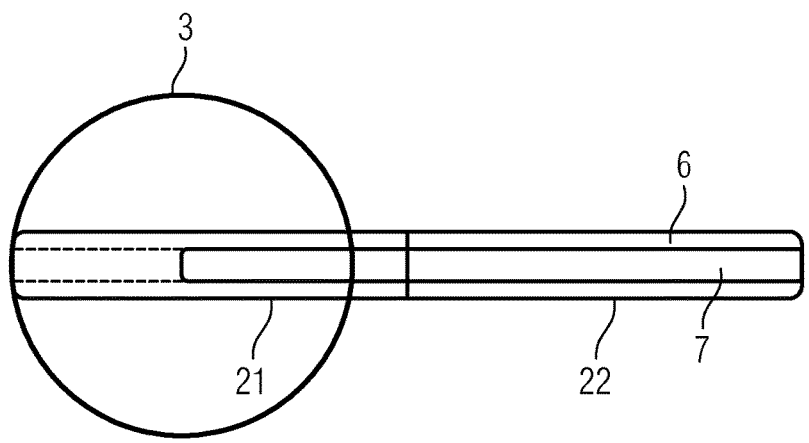
FIG. 4 shows a conventional balloon applicator in cross section.

Beyond the rigid portion 21, the balloon applicator has a flexible portion 22, as is shown in FIG. 4. The first part 2a and the second part 2b of the shaft 2 are enclosed by the rigid portion 21. The flexible portion 22 is ideally longer than the rigid portion 21, since it is intended, during treatment, to be located in a biopsy channel, for example, and outside the patient's body, while the rigid portion 21 is intended to be located in a tissue cavity.

As is shown in FIGS. 2 and 3, the inner core 32 moreover has at least one depression 35 at the holding point 11, which depression 35, with a form fit, matches a protuberance 42 in the second lumen 7. The shape of the depression 35 is polygonal, such that slip-resistant edges are present. The inner core 32 of the tool 30 can thus be applied to the holding point 11 and effect a rotational movement about its longitudinal axis, and thus also a rotational movement of the shaft 2 about the longitudinal axis thereof, without slipping from the holding point. The second lumen 7 has, at the holding point, at least one depression and the inner core 32 has at least one protuberance, and these match each other with a form fit. The protuberances and depressions can expediently be present in any desired number, preferably 1-10, likewise preferably 2-9, likewise preferably 3-8, likewise preferably 4-7, and likewise preferably 5 or 6.

Figure 5:
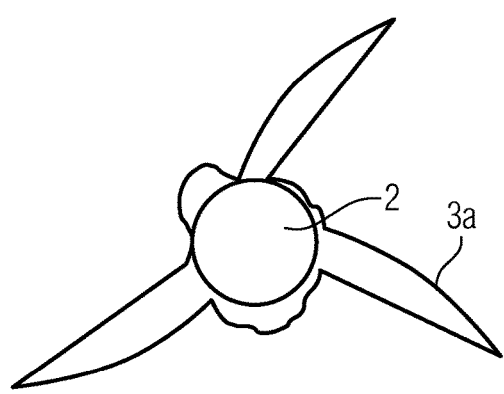
FIG. 5 shows a conventional balloon applicator, seen from the proximal side.

When the balloon 3 is emptied of medium, it lies in folds 3a, as is shown in FIG. 5. The folds of the emptied balloon 3a have to be laid on the shaft 2 or drawn smooth, so that the balloon 3 can be removed from the tissue cavity.

In order to lay the balloon 3 of the balloon applicator 1 around the shaft 2, the second part 2b of the shaft 2 can be fixed with the outer tube 31 of the tool 30, and a torsional moment can be applied to the first part 2a of the shaft 2 relative to the second part 2b in the direction of the rotational movement 8 by means of the inner core 32. For this purpose, after removal of a radiation source from the second lumen 7, the tool 30 is inserted into the second lumen 7, the outer tube 31 is connected with a form fit to the second part of the shaft 2b by means of the protuberance 33 in the depression 41 in the second lumen 7, and the inner core 32 is connected with a form fit to the proximal part 2a of the shaft by means of the protuberance 34 in the depression 43. By a rotational movement 8 of the inner core 32 and the torsional moment thus acting on the first portion of the shaft 2a, the predetermined breaking point 10 breaks, as a result of which a relative movement of the first portion 2a relative to the second portion of the shaft 2b is permitted. The balloon 3 is laid around the shaft 2 by a further rotational movement 8 of the first portion 2a, effected by means of the inner core 32.

If the balloon is to be laid upon the shaft by being drawn smooth, this can be achieved by a linear movement effected with the tool 30. For this purpose, the inner core 32 with the depression 35 at the holding point 11 is connected with a form fit to the protuberance 42 in the second lumen 7 and is used as an abutment, the outer tube 31 is connected with a form fit via the protuberance 36 to the depression 44 in the lumen 7 at the holding point 12, and a tensile force is applied to the outer tube in the distal direction. The acting force causes the material of the shaft 2 to break at the predetermined breaking point 10. This linear movement 9 is shown by way of example in FIG. 1. By pulling further in the direction of the holding point 12, the parts 2a and 2b are drawn apart from each other and the balloon is drawn smooth.

Alternatively, the balloon can also be stretched in the proximal direction. For this purpose, the inner core 32 is connected with a form fit via its depression 35 to the protuberance 42 at the first holding point 11 and is pressed in the direction of the holding point 11. At the holding point 12, the outer tube 31 of the tool 30 is connected with a form fit to the depression 44 via its protuberance 36, in order to fix the distal portion 2b, so as to ensure that the entire balloon applicator is not pushed further into the tissue by the force acting on the holding point 11. The acting force causes the material of the shaft 2 to break at the predetermined breaking point 10. By pressing further in the direction of the holding point 11, the parts 2a and 2b are drawn apart from each other and the balloon 3 is drawn smooth. It is also possible simultaneously to combine pressing at the holding point 11 and pulling at the holding point 12.

It is also possible to first of all break the material of the shaft 2 between first portion 2a and second portion 2b by a torsional moment 8 of the inner core 32 and then to draw the balloon smooth by pressing and/or pulling by means of the inner core 32 in the proximal or distal longitudinal direction of the shaft 2. The rotational movement 8 effected by the torsional moment can also be continued further.

If the connection between the first portion 2a and the second portion 2b of the shaft 2 is in the form of a thread turn, a rotational movement 8 about the longitudinal axis of the shaft 2 and a longitudinal movement 9 along the longitudinal axis of the shaft 2 are effected simultaneously, as a result of which the balloon 3 is simultaneously wound around the shaft 2 and laid along the shaft 2.

Modifications and amendments of the invention that are obvious to a person skilled in the art fall within the scope of protection of the claims.

LIST OF REFERENCE SIGNS 1 balloon applicator
2 shaft
2a first portion of the shaft
2b second portion of the shaft
3 balloon
3a emptied balloon
4 proximal connection position of balloon and shaft
5 distal connection position of balloon and shaft
6 first lumen
7 second lumen
8 indication of the rotational movement
9 indication of the longitudinal movement
10 predetermined breaking point
11 first holding point
12 second holding point
21 rigid portion of the shaft
22 flexible portion of the shaft
30 tool
31 outer tube of the tool
32 inner core of the tool
33 protuberance of the outer tube
34 protuberance of the inner core
35 depression of the inner core
36 protuberance of the outer tube
40 system of balloon applicator and tool
41 depression in the second lumen of the balloon applicator
42 protuberance in the second lumen of the balloon applicator
43 depression in the second lumen of the balloon applicator
44 depression in the second lumen of the balloon applicator

The invention claimed is:

1. A system comprising:
a balloon applicator for irradiation of a cavity within living tissue, comprising an at least double-lumen shaft with a first lumen for introduction of a medium for filling a balloon connected to the shaft at a proximal and a distal position thereof, and with a second lumen for insertion of a radiation source, wherein
the shaft, between the proximal and the distal position, has a proximally arranged first portion and a distally arranged second portion which, in a first working state of the balloon applicator, are connected to each other and, in a second working state of the balloon applicator, are separated from each other; and a tool comprising an outer tube and an inner core mounted movably in the outer tube, wherein the tube is configured to apply a force to a first part of the shaft and/or second part of the shaft of the balloon applicator, wherein the tool is configured to apply a longitudinal force and/or a torsional moment in order to break a predetermined breaking point of the shaft.

2. A method for smoothing folds of a balloon arranged on a shaft of a balloon applicator within living tissue, the method comprising:

exerting a force onto the shaft causing the shaft to break, wherein after the shaft is broken, a first and second part of the shaft are moveable relative to each other;

moving the first part of the shaft relative to the second part of the shaft; and positioning the balloon around or upon the shaft of the balloon applicator.

3. A balloon applicator for irradiation of a cavity within living tissue, comprising an at least double-lumen shaft with a first lumen for introduction of a medium for filling a balloon connected to the shaft at a proximal and a distal position thereof, and with a second lumen for insertion of a radiation source, wherein the shaft, between the proximal and the distal position, has a proximally arranged first portion and a distally arranged second portion which, in a first working state of the balloon applicator, are connected to each other and, in a second working state of the balloon applicator, are separated from each other, and wherein the shaft, in a boundary section between the first and the second portion of the shaft, has a predetermined breaking point which is designed to break when a defined longitudinal force and/or a torsional moment are/is exceeded.

4. The balloon applicator as claimed in claim 3, in which the first portion of the shaft comprises the proximal position and the second portion of the shaft comprises the distal position, at which the balloon is respectively secured on the shaft.

5. The balloon applicator as claimed in claim 3, in which the shaft, in the boundary section between the first and second portion, has a seal which is designed to seal the first and second lumen of the shaft in the second working state of the balloon applicator.

6. The balloon applicator as claimed in claim 3, wherein the second lumen comprises a tool removably inserted into the second lumen, wherein the tool is designed to apply at least one force to the first portion of the shaft and/or second portion of the shaft.

7. The balloon applicator as claimed in claim 6, in which the second or first portion of the shaft is fixed by the tool, and a torsional moment acting relative to the second or first portion of the shaft in a rotational direction about a longitudinal axis of the first portion is applied by the tool to the first or second portion of the shaft.

8. The balloon applicator as claimed in claim 6, in which the first or second portion of the shaft is fixed by the tool, and a force acting relative to the first or second portion of the shaft in a longitudinal direction of the shaft is applied by the tool to the second or first portion of the shaft.

9. The balloon applicator as claimed in claim 6, in which the second lumen has at least one depression or protuberance in which the tool engages with a form fit via the at least one protuberance or depression.

10. The balloon applicator as claimed in claim 6, in which the second lumen has at least one holding point for receiving the tool.

11. The balloon applicator as claimed in claim 3, in which the shaft has a rigid and a flexible portion.

12. A tool comprising:

an outer tube and an inner core mounted movably in the outer tube, wherein the tube is configured to apply a force to a first part of the shaft and/or second part of the shaft of the balloon applicator of claim 11, wherein the tool is configured to apply the longitudinal force and/or the torsional moment in order to break the predetermined breaking point of the shaft, wherein the outer tube has at least one protuberance or depression which, with a form fit, matches at least one depression or protuberance in the second lumen of the balloon applicator.

13. The tool of claim 12, wherein the inner core has at least one protuberance or depression which, with a form fit, matches at least one depression or protuberance in the second lumen of the balloon applicator.

14. A balloon applicator for irradiation of a cavity within living tissue, comprising an at least double-lumen shaft with a first lumen for introduction of a medium for filling a balloon connected to the shaft at a proximal and a distal position thereof, and with a second lumen for insertion of a radiation source, wherein the shaft, between the proximal and distal position, has a proximally arranged first portion and a distally arranged second portion which, in a first working state of the balloon applicator, are connected to each other and, in a second working state of the balloon applicator, are separated from each other, and wherein the shaft, in a boundary section between the first and the second portion, has a connection with a thread turn.

15. The balloon applicator as claimed in claim 14, in which the first portion of the shaft comprises the proximal position and the second portion of the shaft comprises the distal position, at which the balloon is respectively secured on the shaft.

16. The balloon applicator as claimed in claim 14, wherein the second lumen comprises a tool removably inserted into the second lumen, wherein the tool is designed to apply at least one force to the first portion of the shaft and/or second portion of the shaft.

17. The balloon applicator as claimed in claim 16, in which the second or first portion of the shaft is fixed by the tool, and a torsional moment acting relative to the second or first portion of the shaft in a rotational direction about a longitudinal axis of the first portion is applied by the tool to the first or second portion of the shaft.

18. The balloon applicator as claimed in claim 16, in which the first or second portion of the shaft is fixed by the tool, and a force acting relative to the first or second portion of the shaft in a longitudinal direction of the shaft is applied by the tool to the second or first portion of the shaft.

* * * * *